US008343519B2

(12) United States Patent
Hansenne et al.

(10) Patent No.: US 8,343,519 B2
(45) Date of Patent: Jan. 1, 2013

(54) CHEMICAL ENHANCER AND METHOD

(75) Inventors: Isabelle Hansenne, Westfield, NJ (US); Marc Cornell, Jackson, NJ (US); Hani Fares, Somerset, NJ (US); Sidney P. Foltis, Nutley, NJ (US)

(73) Assignee: L'Oreal S.A., Paris (FR)

( * ) Notice: Subject to any disclaimer, the term of this patent is extended or adjusted under 35 U.S.C. 154(b) by 838 days.

(21) Appl. No.: 10/367,700

(22) Filed: Feb. 19, 2003

(65) Prior Publication Data
US 2004/0162272 A1 Aug. 19, 2004

(51) Int. Cl.
*A61K 31/60* (2006.01)
*A61K 9/00* (2006.01)

(52) U.S. Cl. ........................................ 424/401; 514/165
(58) Field of Classification Search .................. 424/401; 514/165
See application file for complete search history.

(56) References Cited

U.S. PATENT DOCUMENTS

| 4,767,750 | A | * | 8/1988 | Jacquet et al. ................. 514/159 |
| 5,164,185 | A | | 11/1992 | Charpin et al. |
| 5,267,407 | A | | 12/1993 | Bornancini |
| 5,443,823 | A | | 8/1995 | Rosenbaum et al. |
| 5,516,793 | A | * | 5/1996 | Duffy ............................ 514/474 |
| 5,554,654 | A | | 9/1996 | Yu et al. |
| 5,558,871 | A | | 9/1996 | Griat et al. |
| 5,561,157 | A | | 10/1996 | Yu et al. |
| 5,580,549 | A | | 12/1996 | Fukuda et al. |
| 5,629,015 | A | * | 5/1997 | Ribier et al. |
| 5,660,839 | A | * | 8/1997 | Allec et al. ..................... 424/401 |
| 5,665,776 | A | | 9/1997 | Yu et al. |
| 5,667,789 | A | | 9/1997 | Collin et al. |
| 6,159,479 | A | | 12/2000 | Pinzon |
| 6,200,964 | B1 | * | 3/2001 | Singleton et al. .............. 514/159 |
| 6,267,972 | B1 | | 7/2001 | Breton et al. |
| 6,586,020 | B1 | | 7/2003 | Breton et al. |

FOREIGN PATENT DOCUMENTS

| EP | 0 378 936 | 7/1990 |
| EP | 0 570 230 | 11/1993 |
| EP | 0-679-388 | 2/1996 |
| EP | 0-909-556 | 4/1999 |
| EP | 1 214 925 | 6/2002 |
| FR | 2581 542 | 11/1986 |
| WO | WO 97/02876 | 8/1997 |

OTHER PUBLICATIONS

Remington Pharmaceutical Sciences, 17th ed., 1985, p. 1513-1514.*
A Comparative Ultrastructural Study of Hydroxyacids Induced Desquamation, EJD No. 4, vol. 12, Jul.-Aug. 2002, P. Corcuff, 5 pp.
Plentitude Activ Futur Creme Peaux Seches SPF8 Formulation (Jul. 2001).

* cited by examiner

*Primary Examiner* — San-Ming Hui
(74) *Attorney, Agent, or Firm* — Oblon, Spivak, McClelland, Maier & Neustadt, L.L.P.

(57) ABSTRACT

The present invention relates to compositions containing at least one salicylic acid derivative and at least one cosmetic, dermatologic, pharmaceutical, etc. active agent, where the salicylic acid derivative increases, enhances, etc., the efficacy of the active agent, as well as to methods of making and using such compositions. The invention further relates to a method for enhancing the efficacy of active agents with these salicylic acid derivatives.

32 Claims, No Drawings

CHEMICAL ENHANCER AND METHOD

BACKGROUND OF THE INVENTION

1. Field of the Invention

The present invention relates to compositions comprising at least one salicylic acid derivative and at least one cosmetic, dermatologic, pharmaceutical, etc. active agent, where the salicylic acid derivative increases, enhances, etc., the efficacy of the active agent, as well as to methods of making and using such compositions. The invention further relates to a method for enhancing the efficacy of active agents with these salicylic acid derivatives.

2. Background of the Invention

The intact skin of humans is a very effective barrier to many natural and synthetic substances. Active agents may be pharmacologically effective by systemic administration, but many of them are much less or totally ineffective upon application to the skin. The effectiveness of an active agent can depend on at least two major factors: a) percutaneous absorption and penetration, and b) bioavailability of the penetrated agent to the target site in the skin. To be effective, a pharmaceutical drug must penetrate the stratum corneum into the epidermal layers, and distribute and be bioavailable to the target sites for action. Many active agents may possess inherent characteristics which may prohibit them from effectively penetrating the skin or prohibit them from being bioavailable to the target sites in the skin. Therefore, the efficacy of such agents may be minimal and ineffective.

Accordingly, a need exists for boosters of active agents that provide increased efficacy, improved therapeutic results, etc.

DETAILED DESCRIPTION OF THE PRESENT INVENTION

All publications, patent applications, patents, and other references and documents mentioned herein are incorporated herein by reference in their entirety. Unless specifically defined, all technical and scientific terms used herein have the same meaning as commonly understood by a skilled artisan in biochemistry, chemistry, cosmetology, dermatology, pharmaceutical science, and materials science.

All methods and materials similar or equivalent to those described herein can be used in the practice or testing of the present invention, with suitable methods and materials being described herein. Further, the materials, methods, and examples are illustrative only and are not intended to be limiting.

While not bound by a particular theory, the chemical boosters of the invention may be efficacious by acting to enhance the penetration of an active agent into the skin, and/or by increasing the bioavailability of the active agent.

The present invention provides a method for enhancing, increasing, etc. the efficacy of an active agent (e.g., a cosmetic and/or pharmaceutical and/or dermatological active agent) by using, in combination with the active agent, at least one salicylic compound of formula (I):

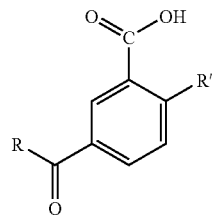

where

R is a linear, branched or cyclic saturated aliphatic group or an aliphatic unsaturated group containing one or a number of double bonds, which may or may not be conjugated, these groups containing from 2 to 22 carbon atoms and being able to be substituted by at least one substituent selected from (a) halogen atoms, (b) the trifluoromethyl group, (c) hydroxyl groups in the free form or esterified by an acid having from 1 to 6 carbon atoms or (d) a carboxyl functional group which is free or esterified by a lower alcohol having from 1 to 6 carbon atoms;

R' is a hydroxyl group or an ester functional group of formula

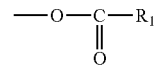

where $R_1$ is a linear or branched saturated or unsaturated aliphatic group having from 1 to 18 carbon atoms, and salts thereof.

In a preferred embodiment R is a linear, branched or cyclized saturated aliphatic chain containing from 3 to 11 carbon atoms, an unsaturated chain containing from 3 to 17 carbon atoms and containing one or more conjugated or unconjugated double bonds, the abovementioned chains being optionally substituted by one or more halogen atoms or by trifluoromethyl groups, by one or more hydroxyl groups in free form or esterified by an acid containing from 1 to 6 carbon atoms, or by a carboxyl group, free or esterified by a lower alcohol containing from 1 to 6 carbon atoms, these various groups being optionally simultaneously present in the said substituents; and R' is a hydroxyl group or an ester group of formula

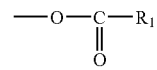

where $R_1$ is a saturated or unsaturated aliphatic group containing from 1 to 18 carbon atoms.

The present invention also provides a method for increasing or enhancing the bioavailability and/or the percutaneous absorption and/or penetration of an active agent by using, in combination with the active agent, at least one of the abovementioned salicylic compounds having the above-mentioned formula (I).

As used herein, "in combination" includes in the same composition, as well as separate overlapping applications to, e.g., the skin, of each ingredient in any order.

The present invention also provides methods of making compositions by physically combining, blending, contacting, etc. in any order of addition (hereinafter "mixing") at least one salicylic acid derivative of Formula 1 as described above and at least one active agent. The resultant compositions also make up a part of the invention, where the salicylic acid derivative is present in an amount that enhances or increases the efficacy of the active agent.

Preferred salicylic acid derivatives useful herein include those described in U.S. Pat. Nos. 6,159,479 and 5,558,871, FR 2,581,542, U.S. Pat. No. 4,767,750, EP 378,936, U.S. Pat. Nos. 5,267,407, 5,667,789, 5,580,549, and EP-A-570,230, all incorporated herein by reference. Further, particularly preferred salicylic acid derivatives useful herein include 5-n-octanoyl salicylic acid (capryloyl salicylic acid), 5-n-decanoyl salicylic acid, 5-n-dodecanoyl salicylic acid, 5-n-heptyloxy salicylic acid and 4-n-heptyloxy salicylic acid. A highly preferred salicylic acid derivative is capryloyl salicylic acid (Trade name: Mexoryl SAB); see page 139 of the International Cosmetic Ingredient Dictionary, 6th Edition, Volume 1, published by the Cosmetic Toiletries, and Fragrance Association, 1995, incorporated herein by reference.

With regard to formula I above, the R group contains from 2 to 22 carbon atoms, inclusive of each and every carbon atom in between this range, including subranges. Useful carbon numbers include 4, 6, 8, 10, 12, 14, 16, and 18. For the R' group of formula I above, each and every carbon number between 1 and 18 is specifically included, and as are all subranges. Useful carbon numbers include 2, 4, 6, 8, 10, 12, 14, and 16. All odd carbon numbers between 2 and 22 carbon atoms for R, and all odd numbered carbon numbers between 1 and 18 for R', are also specifically included.

Useful salts of the invention salicylic acid derivative may be obtained by salification with a base. Useful bases include inorganic basis such as alkali and alkaline metal hydroxides (sodium hydroxide, potassium hydroxide, and the like) or ammonia hydroxides. Organic bases may also be used for salification. Also useful are amphoteric bases. See U.S. patent application Ser. No. 08/627,965, incorporated herein by reference, for useful salicylic acid derivatives and useful salts thereof. Quatermium salts such as dimethylhydroxypropyl ammonium salts are also particularly useful.

In the present invention, the compositions comprise the at least one salicylic acid derivative of the invention at a concentration of at least 0.01 wt %, preferably from 1 wt % to 99 wt % including all values and subranges therebetween such as 2, 5, 10, 15, 20, 25, 30, 35, 40, 45, 50, 55, 60, 65, 70, 75, 80, 85, 90, and 95 wt %. In all cases the at least one salicylic acid derivative of the invention is present in an amount that increases, enhances, etc (hereinafter "enhances") the efficacy of the active agent used or present in combination therewith. Where the salicylic acid derivative(s) is applied by itself, either before, after, or simultaneously with a separate overlapping (e.g., to the same site, or applied, at least in part, over one another) application of the active agent, the salicylic acid derivative is applied in an amount sufficient to obtain the desired effect, i.e., enhancement of the efficacy of the active agent, this amount being available to one of skill in the art in view of this disclosure based on his/her knowledge of the active agent's efficacy in the absence of and in the presence of the present invention contribution to the art, the determination of which is easily within the skill of the ordinary artisan in view of this disclosure.

A dermatologically acceptable carrier may also be employed in the compositions of the invention and/or in the application of the invention salicylic acid derivatives and/or active agents. A group of preferred carriers include, for example, dermatologically acceptable liquid solvents in which the salicylic acid derivatives are soluble, preferably at high concentrations. The term "dermatologically acceptable liquid solvents" is intended to mean those solvents which can safely be used on the skin in the topical treatment methods of this invention, i.e., solvents which do not provoke a severe reaction and which are not toxic when contacted with the skin for relatively short periods of time. Examples of preferred solvents include water, alkylene glycols such as propylene glycol, glycolic acid, and aqueous alcohol. Highly preferred solvents include ethanol and isopropanol. Other useful solvents include acetone, ether (diethyl ether). Mixtures containing one or more of these solvents or other solvents listed above may also be used.

As indicated above, invention materials may contain water. It is important to note that the above-mentioned dermatologically acceptable liquid solvents, whether preferred or not, may be utilized alone or in combination with one another.

Other useful carriers herein include the various dermatological and cosmetic carriers such as gels, emulsions, creams, waxes, compacts, etc.

As mentioned above, the present invention provides methods of enhancing the efficacy of an active agent. While not bound by a theory, this enhancement may occur for example by enhancing the bioavailability, the percutaneous absorption, and/or the penetration of the active agent. Further, the invention relates to compositions comprising at least one salicylic acid derivative of formula 1 and at least one active agent, where the at least one salicylic acid derivative of formula 1 is present in an amount effective to enhance the efficacy of at least one active agent present.

Examples of active agents useful herein include, for example, age spot agents, keratose removing agents, analgesic, anesthetic, antiacne agents, antibacterial, antiyeast agents, antifungal agents, antiviral agents, antiburn agents, antidandruff agents, antidermatitis agents, antipruritic agents, antiperspirant, antiinflammatory agents, antihyperkeratolytic agents, antidryskin agents, antpsoriatic agents, antiseborrheic agents, astringent, softener, emollient agents, coal tar, bath oil, sulfur, rinse conditioner, foot care agents, fungicide, hair growth promoter, hair remover, keratolytic agents, moisturizer agents, powder, shampoo, skin bleach, skin protectant, soap, cleanser, antiaging agents, sunscreen agents, wart remover, wet dressing, vitamin, tanning agents, topical antihistamine agents, hormone, vasodilator, retinoid, bronchial dilator, and topical cardiovascular agents.

Preferred active agents include agents (1) to (13) below:

1) Agents which modify cutaneous differentiation and/or proliferation and/or pigmentation such as retinoic acid and isomers thereof, retinol and esters thereof, vitamin D and compounds thereof, estrogens such as estradiol, kojic acid or hydroquinone;
(2) Antibacterial agents such as clindamycin phosphate, erythromycin or antibiotics from the tetracycline family;
(3) Antiparasitic agents, in particular metronidazole, crotamiton or pyrethroids;
(4) Antifungal agents, in particular compounds of the imidazole family such as econazole, ketoconazole or miconazole or salts thereof, polyene compounds such as amphotericin B, compounds of the allylamine family, such as terbinafine, or alternatively octopirox;
(5) Steroidal anti-inflammatory agents such as hydrocortisone, betamethasone valerate or clobetasol propionate, or nonsteroidal anti-inflammatory agents such as ibuprofen and salts thereof, diclofenac and salts thereof, acetylsalicylic acid, acetaminophen or glycyrrhetinic acid;
(6) Anaesthetic agents such as lidocaine hydrochloride and compounds thereof;
(7) Antipruriginous agents such as thenaldine, trimeprazine or cyproheptadine;
(8) Antiviral agents such as acyclovir;
(9) Keratolytic agents such as alpha- and beta-hydroxycarboxylic acids or beta-ketocarboxylic acids, salts, amides or esters thereof and more particularly hydroxy acids such as glycolic acid, lactic acid, salicylic acid, citric acid and fruit acids in general, and 5-n-octanoylsalicylic acid;
(10) Anti-free-radical agents such as alpha-tocopherol or esters thereof, superoxide dismutases, certain metal-chelating agents or ascorbic acid and esters thereof,
(11) Antiseborrhoeic agents such as progesterone;
(12) Antidandruff agents such as octopirox or zinc pyrithione;

(13) Antiacne agents such as retinoic acid or benzoyl peroxide.

Other useful active agents are found in U.S. Pat. Nos. 5,665,776, 5,561,157, and 5,554,654, all incorporated herein by reference. Of course, combinations of active agents may be used herein.

The present invention preferably uses the active agent in concentrations of at least 0.01 wt %, preferably from 1 wt % to 99 wt %, including all values and subranges therebetween, such as 2, 5, 10, 15, 20, 25, 30, 35, 40, 45, 50, 55, 60, 65, 70, 75, 80, 85, 90, and 95 wt %. Where the active agent(s) is applied by itself, either before, after, or simultaneously with a separate application of the salicylic acid derivative, the agent is applied in an amount sufficient to obtain the desired effect, this amount being available to one of skill in the art based on knowledge of the active agent's increased efficacy in view of the present invention contribution to the art, the determination of which is easily within the skill of the ordinary artisan in view of this disclosure.

The compositions of the present invention may be prepared by mixing one or more invention salicylic acid derivatives with the active agent. If used in separate applications the salicylic acid derivative and/or active agent may themselves be formulated with, e.g., a carrier, preferably a dermatologically acceptable liquid solvent.

The salicylic acid derivative and active agent used may be in any form.

The compositions of the invention may of course comprise other components, such as preservatives, stabilizers, antioxidants, thickening agents, surfactants, pigments, colorants, fragrances and other adjuvants. Such components are preferably dermatologically acceptable. Preferably, the additional components do not interfere with the efficacy or impose any negative influence upon the efficacy of the active agent. Such additives may further include, for example, an aromatic, a surfactant, a preservative, an anti-oxidant, a moisturizing agent, and so on. Of course the additional components may be present individually or in combination, and their concentrations are not limited.

Other useful additives may include compounds having formula (II)

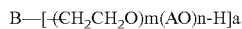

B—[-(CH$_2$CH$_2$O)m(AO)n-H]a wherein B is an alcohol residue,
AO is an alkylene-oxy group having from 3 to 18 carbon atoms
a in an integer that is greater than or equal to 1,
m is an integer that is greater than or equal to 4,
n is an integer that is greater than or equal to 0,
provided that a molar amount m of the ethylene oxide to be added is a value that amounts to at least 40% or the entire molecular weight of the ethylene oxide chain moiety.

In the above general formula II, the alcohol to be represented by reference symbol B is intended to mean a monovalent alcohol including, for example, an alkyl alcohol such as ethanol, butanol, lauryl alcohol, myristyl alcohol, palmityl alcohol, stearyl alcohol, cetyl alcohol, etc., and an alkenyl alcohol such as linoleyl alcohol, palmitoyl alcohol, oleyl alcohol, etc., a divalent alcohol such as ethylene glycol, propylene glycol, etc., a trivalant alcohol such as glycerin, trimethylol propane, triethanol amine, etc., a tetravalent alcohol such as pentaerythritol, diglycerin, etc. There may also be used other polyvalent alcohols such as sorbitol, polyglycerin and so on.

The alkyleneoxy group having 3 to 18 carbon atoms, as referred to by reference symbol AO, may include, for example, propyleneoxy, butyleneoxy, tetrahydrofuran, α-olefinoxy, and so on. The alkyleneoxy groups having 3 and 4 carbon atoms, such as oxidopropylene, oxidobutylene and tetrahydrofuran, are preferred.

In the above general formula, reference symbol "a" is an integer of 1 or more. When the alcohol to be used for the present invention is a monovalent alcohol, the reference symbol "a" is 1. When the alcohol to be used therefore is a divalent alcohol, the reference symbol "a" is 2. Likewise, when the alcohol to be used therefore is a trivalent alcohol, the reference symbol "a" is 3. Further, when the alcohol to be used therefore is a polyvalent alcohol, the reference symbol "a" is the integer corresponding to the valence of the alcohol used.

In the above general formula, reference symbol "m" is intended to mean an average molar amount of ethylene oxide to be added. The number of a polymerization chain of the ethylene oxide has to be at least 4.

Reference symbol "n" is intended to mean an average molar amount of an oxidized alkylene to be added. The number of a polymerization chain of the oxidized alkylene is zero or 1 or more.

The manner of polymerization of the ethylene oxide and the alkylene oxide is random or block polymerization.

The molar amount m of the ethylene oxide to be added is set to amount to 40% or more of the entire molecular weight of the ethylene oxide chain. This setting is based on the fact that, if the molar amount m of the ethylene oxide to be added would be less than the above molar amount, the phenol compound such as salicylic acid derivative would become unlikely to be sustained in the polyethylene glycol compound.

The additive compounds having formula II may be synthesized in a conventional manner, for example, by reacting the ethylene oxide and the alkylene oxide with the alkyl alcohol or the alkenyl alcohol under an inert gas such as nitrogen or the like in the presence of a basic catalyst such as sodium hydroxide, potassium hydroxide or the like or an acidic catalyst such as boron tetrafluoride, tin tetrachloride or the like.

Specific examples of the additive compounds having formula II are discussed in EP 1 214 925 A1, incorporated herein by reference.

The combination of active agent and salicylic acid derivative is applied to the skin, body, eyes, etc, where the active agent is expected to have its effect, including the hair, lips, mucuous membranes, inteugments, scalp, eyes, etc. (hereinafter "the body") and allowed to remain there for action in or on the body.

The composition of the present invention may be in cream or ointment form containing at least one of salicylic acid derivative and at least one active agent. These components may be initially dissolved in a solvent such as water, ethanol, acetone, propylene glycol or polysorbate 80. The solution may then be mixed in a conventional manner with commonly available cream or ointment base such as hydrophilic ointment or petrolatum.

Compositions of the instant invention may also be formulated in gel, lotion, shampoo, spray, stick or powder. An example of one gel composition of the instant invention utilizes at least one of salicylic acid derivative and at least one active agent dissolved in a mixture of ethanol, water and propylene glycol in a volume ratio of 40:40:20, respectively. A gelling agent such as hydroxyethylcellulose, hydroxypropylcellulose, hydroxypropylmethylcellulose or ammoniated glycyrrhizinate may then added to the mixture with agitation. The preferred concentration of the gelling agent may range from 0.1 to 4 percent by weight of the total composition.

The present invention is explained in more detail with the aid of the following embodiment examples. Percents are weight percents based on total weight unless otherwise specified. Although the examples utilize only selected compounds and formulations, it should be understood that the following examples are illustrative and not limited. Of course, any of the aforementioned salicylic acid derivatives and active agents may be substituted according to the teachings of this invention in the following examples.

EXAMPLES

Example 1

Lotion with Kojic Acid

Kojic Acid 1%/Caployl salicylic acid 2%/EDTA 0.1%/ Ethanol 40%/Water Qs 100%

Example 2

| Cream with Hydroquinone | | |
|---|---|---|
| Phase A | water | QS 100% |
| | Preservative, sequestrant, anti-oxidant | 0.4% |
| | Glycerin | 23% |
| | Hydroquinone | 4% |
| | Capryloyl salicylic acid | 1% |
| | Propylene glycol | 6% |
| Phase B | Cyclopentasiloxane (and) PEG/PPG-18/18 Dimethicone | 20% |
| | Dimethicone (and) dimethicone/vinyl dimethicone Crosspolymer | 5% |
| | Preservative | 0.1% |

Example 3

| Lotion with Hydrocortisone | |
|---|---|
| Caprolactame | 46% |
| Ethanol | 46% |
| Hydrocortisone | 2% |
| Capryloyl salicylic acid | 3% |
| Glycerine | 3% |

Example 4

| Cream with Vitamin C | | |
|---|---|---|
| Phase A | water | QS 100% |
| | Preservative, sequestrant, anti-oxidant | 0.4% |
| | Glycerin | 23% |
| | Magnesium ascorbyl phosphate | 5% |
| | Capryloyl salicylic acid | 1% |
| | Propylene glycol | 6% |
| Phase B | Cyclopentasiloxane (and) PEG/PPG-18/18 Dimethicone | 20% |
| | Dimethicone (and) dimethicone/vinyl dimethicone Crosspolymer | 5% |
| | Preservative | 0.1% |

Example 5

| Cream with Retinol | | |
|---|---|---|
| Phase A | water | QS 100% |
| | Preservative, sequestrant, anti-oxidant | 0.4% |
| | Glycerin | 23% |
| | Retinol | 0.25% |
| | Capryloyl salicylic acid | 1% |
| | Propylene glycol | 6% |
| Phase B | Cyclopentasiloxane (and) PEG/PPG-18/18 Dimethicone | 20% |
| | Dimethicone (and) dimethicone/vinyl dimethicone Crosspolymer | 5% |
| | Preservative | 0.1% |

The above specification provides a written description of the invention, and of the manner and process of making and using it, in such full, clear, concise, and exact terms as to enable any person skilled in this art to make and use the same, this description and enablement including that for a method of enhancing the efficacy of an active agent in or on the body, comprising applying to the body a combination of an active agent and at least one salicylic acid derivative of formula (I) in an amount effective to enhance the efficacy of the active agent:

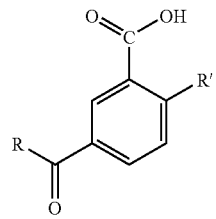

wherein

R is a linear, branched or cyclic saturated aliphatic group or an aliphatic unsaturated group containing one or a number of double bonds, which may or may not be conjugated, these groups containing from 2 to 22 carbon atoms and being able to be substituted by at least one substituent selected from the group consisting of (a) halogen atoms, (b) a trifluoromethyl group, (c) hydroxyl groups in the free form or esterified by an acid having from 1 to 6 carbon atoms and (d) a carboxyl functional group which is free or esterified by a lower alcohol having from 1 to 6 carbon atoms;

R' is a hydroxyl group or an ester functional group of formula

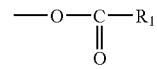

wherein $R_1$ is a linear or branched saturated or unsaturated aliphatic group having from 1 to 18 carbon atoms, and salts thereof, where in a preferred embodiment, the salicylic acid derivative is 5-n-octanoyl-salicylic acid, where the active agent may be selected from, for example, the group consisting of an age spot agents, keratose removing agents, analgesic, anesthetic, antiacne agents, antibacterial, antiyeast agents, antifungal agents, antiviral agents, antiburn agents, antidandruff agents, antidermatitis agents, antipruritic agents, antiperspirant, antiinflammatory agents, antihyperkeratolytic agents, antidryskin agents, antipsoriatic agents, antiseborrheic agents, astringent, softener, emollient agents, coal tar, bath oil, sulfur, rinse conditioner, foot care agents, fungicide, hair growth promoter, hair remover, keratolytic agents, moisturizer agents, powder, shampoo, skin bleach, skin protectant, soap, cleanser, antiaging agents, sunscreen agents, wart remover, wet dressing, vitamin, tanning agents, topical antihistamine agents, hormone, vasodilator, retinoid, bronchial dilator, and topical cardiovascular agents. Further active agents described and enabled herein include retinoic acid, retinoic acid compounds, retinol, retinol ester, vitamin D, vitamin D compounds, estrogen, estradiol, kojic acid, hydroquinone, clindamycin phosphate, erythromycin, erythromycin compound, tetracycline compound, metronidazole, crotamiton, pyrethroids, econazole, ketoconazole miconazole, polyene compound, amphotericin B, allylamine compound, terbinafine, octopirox, steroid, hydrocortisone, betamethasone valerate, clobetasol propionate, nonsteroidal anti-inflammatory agents, ibuprofen, diclofenac, acetylsalicylic acid, acetaminophen, glycyrrhetinic acid, lidocaine hydrochloride, lidocaine hydrochloride compound, thenaldine, trimeprazine, cyproheptadine, acyclovir, keratolytic agents, alpha-hydroxycarboxylic acid, beta-hydroxycarboxylic acid, beta-ketocarboxylic acid, alpha-hydroxycarboxylic acid amide, beta-hydroxycarboxylic acid amide, beta-ketocarboxylic acid amide, alpha-hydroxycarboxylic acid ester, beta-hydroxycarboxylic acid ester, beta-ketocarboxylic acid ester, hydroxy acid, glycolic acid, lactic acid, salicylic acid, citric acid, fruit acid, 5-n-octanoylsalicylic acid, salicylic acid, alpha-tocopherol, alpha-tocopherol ester, superoxide dismutases, metal-chelating agents, ascorbic acid, ascorbic acid ester, progesterone, octopirox, zinc pyrithione, and benzoyl peroxide.

Similarly fully described and enabled is a composition comprising at least one active agent and at least one salicylic acid derivative of formula (I) above in an amount effective to enhance the efficacy of the active agent in or on the body, and a method of making such a composition comprising mixing the at least one salicylic acid derivative with the at least one active agent, as well as a method of using such a composition.

The invention claimed is:

1. A composition in the form of an oil-in-water emulsion comprising water, an active agent and at least one salicylic acid derivative of formula (1) present in an amount and a form effective to enhance the efficacy of the active agent in or on the body:

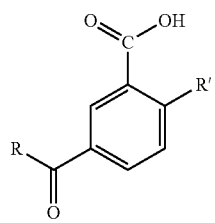

(1)

wherein

R is a linear, branched or cyclic saturated aliphatic group or an aliphatic unsaturated group containing one or a number of double bonds, which may or may not be conjugated, these groups containing from 2 to 22 carbon atoms and being able to be substituted by at least one substituent selected from the group consisting of (a) halogen atoms, (b) a trifluoromethyl group, (c) hydroxyl groups in the free form or esterified by an acid having from 1 to 6 carbon atoms and (d) a carboxyl functional group which is free or esterified by a lower alcohol having from 1 to 6 carbon atoms;

R' is a hydroxyl group or an ester functional group of formula

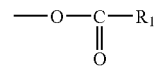

wherein $R_1$ is a linear or branched saturated or unsaturated aliphatic group having from 1 to 18 carbon atoms, and salts thereof, and wherein the active agent and the at least one salicylic acid derivative are present in the solvent, and wherein the active agent is selected from the group consisting of keratolytic agents, benzoyl peroxide, and mixtures thereof.

2. The composition according to claim 1, wherein the salicylic acid derivative is 5-n-octanoyl-salicylic acid.

3. The composition according to claim 1, further comprising a dermatologically acceptable carrier.

4. A method of making the composition according to claim 1, comprising mixing the salicylic acid derivative and the active agent.

5. The composition according to claim 1, wherein the salicylic acid derivative is selected from the group consisting of 5-n-octanoyl-salicylic acid, 5-n-decanoyl-salicylic acid, 5-n-dodecanoyl-salicylic acid, 5-n-heptyloxy-salicylic, 5-n-heptyloxy-salicylic acid, and mixtures thereof.

6. The composition according to claim 1, further comprising a surfactant.

7. The composition according to claim 1, wherein the salicylic acid derivative of formula (1) is present in an amount effective to enhance the penetration of the active agent into skin, an amount effective to increase the bioavailability of the active agent, or both.

8. The composition according to claim 7, wherein the salicylic acid derivative is 5-n-octanoyl-salicylic acid.

9. The composition according to claim 7, further comprising a dermatologically acceptable carrier.

10. A method of making the composition according to claim 7, comprising mixing the salicylic acid derivative and the active agent.

11. The composition according to claim 7, wherein the salicylic acid derivative is selected from the group consisting of 5-n-octanoyl-salicylic acid, 5-n-decanoyl-salicylic acid, 5-n-dodecanoyl-salicylic acid, 5-n-heptyloxy-salicylic, 5-n-heptyloxy-salicylic acid, and mixtures thereof.

12. The composition according to claim 7, further comprising a surfactant.

13. The composition according to claim 1, wherein the salicylic acid derivative is present in an amount ranging from 0.01% to less than 2% by weight with respect to the total weight of the composition.

14. The composition according to claim 1, wherein the salicylic acid derivative is present in an amount ranging from 0.01% to less than about 1% by weight with respect to the total weight of the composition.

15. The composition according to claim 7, wherein the salicylic acid derivative is present in an amount ranging from 0.01% to less than 2% by weight with respect to the total weight of the composition.

16. The composition according to claim 7, wherein the salicylic acid derivative is present in an amount ranging from 0.01% to less than about 1% by weight with respect to the total weight of the composition.

17. The composition according to claim 1, wherein the composition comprises benzoyl peroxide as the active agent.

18. The composition according to claim 1, wherein the composition comprises at least one keratolytic agent as the active agent.

19. The composition according to claim 7, wherein the composition comprises benzoyl peroxide as the active agent.

20. The composition according to claim 7, wherein the composition comprises at least one keratolytic agent as the active agent.

21. The composition according to claim 1 wherein the composition further comprises a silicone oil, a silicone elastomer, or mixtures thereof.

22. The composition according to claim 7, wherein the composition further comprises a silicone oil, a silicone elastomer, or mixtures thereof.

23. The composition according to claim 18, wherein the keratolytic active agent is selected from the group consisting of glycolic acid, lactic acid, salicylic acid, and mixtures thereof.

24. The composition according to claim 20, wherein the keratolytic active agent is selected from the group consisting of glycolic acid, lactic acid, salicylic acid, and mixtures thereof.

25. The composition according to claim 18, wherein the active agent is present in an amount ranging from 1% to 20% by weight with respect to the total weight of the composition.

26. The composition according to claim 18, wherein the active agent is present in an amount ranging from 2% to 10% by weight with respect to the total weight of the composition.

27. The composition according to claim 20, wherein the active agent is present in an amount ranging from 1% to 20% by weight with respect to the total weight of the composition.

28. The composition according to claim 20, wherein the active agent is present in an amount ranging from 2% to 10% by weight with respect to the total weight of the composition.

29. The composition according to claim 18, wherein the keratolytic active agent is selected from the group consisting of glycolic acid, lactic acid, salicylic acid, citric acid, and mixtures thereof.

30. The composition according to claim 21, comprising a component selected from the group consisting of dimethicone, dimethicone/vinyl dimethicone crosspolymer, and mixtures thereof.

31. The composition according to claim 20, wherein the keratolytic active agent is selected from the group consisting of glycolic acid, lactic acid, salicylic acid, citric acid, and mixtures thereof.

32. The composition according to claim 21, comprising a component selected from the group consisting of dimethicone, dimethicone/vinyl dimethicone crosspolymer, and mixtures thereof.

* * * * *